US012616917B2

(12) United States Patent
Augier et al.

(10) Patent No.: US 12,616,917 B2
(45) Date of Patent: \*May 5, 2026

(54) METHOD FOR PURIFYING AN AQUEOUS-ALCOHOLIC FEEDSTOCK COMPRISING ETHANOL AND ACETALDEHYDE

(71) Applicants: IFP Energies Nouvelles, Rueil-Malmaison (FR); Compagnie Générale des Etablissements Michelin, Clermont-Ferrand (FR)

(72) Inventors: Frederic Augier, Rueil-Malmaison (FR); Pierre Olivier Dreger, Rueil-Malmaison (FR)

(73) Assignees: IFP Energies Nouvelles, Rueil-Malmaison Cedex (FR); Compagnie Générale des Etablissements Michelin, Clermont-Ferrand (FR)

( \* ) Notice: Subject to any disclaimer, the term of this patent is extended or adjusted under 35 U.S.C. 154(b) by 704 days.

This patent is subject to a terminal disclaimer.

(21) Appl. No.: 17/605,617

(22) PCT Filed: Apr. 6, 2020

(86) PCT No.: PCT/EP2020/059739
§ 371 (c)(1),
(2) Date: Oct. 22, 2021

(87) PCT Pub. No.: WO2020/216603
PCT Pub. Date: Oct. 29, 2020

(65) Prior Publication Data
US 2022/0226749 A1 Jul. 21, 2022

(30) Foreign Application Priority Data

Apr. 25, 2019 (FR) ...................................... 1904345

(51) Int. Cl.
*C07C 29/86* (2006.01)
*B01D 11/04* (2006.01)
*C07C 45/80* (2006.01)

(52) U.S. Cl.
CPC ...... *B01D 11/0426* (2013.01); *B01D 11/0488* (2013.01); *B01D 11/0492* (2013.01); *C07C 29/86* (2013.01); *C07C 45/80* (2013.01)

(58) Field of Classification Search
CPC .................... C07C 29/74–86; C07C 45/78–80
See application file for complete search history.

(56) References Cited

U.S. PATENT DOCUMENTS 10,463,987 B2 11/2019 Hognon et al.
2019/0232193 A1 8/2019 Hognon et al.

FOREIGN PATENT DOCUMENTS

FR 3057467 A1 4/2018
WO 2017/194559 A1 11/2017
(Continued)

OTHER PUBLICATIONS

Machine translation of Patent No. FR3057467A1, Apr. 20, 2018; pp. 1-8 (Year: 2018).\*
(Continued)

*Primary Examiner* — Medhanit W Bahta
(74) *Attorney, Agent, or Firm* — Csaba Henter; MILLEN, WHITE, ZELANO & BRANIGAN

(57) ABSTRACT

The invention concerns a method for purifying a hydroalcoholic feedstock, comprising: a) a step of counter-current liquid-liquid extraction, comprising an extraction section supplied at the top with said hydroalcoholic feedstock and at least one intermediate raffinate fraction from step b) and at the bottom with an extraction solvent, and producing at the top an extraction stream and at the bottom a raffinate, wherein the extraction section is operated at a mean tem-
(Continued)

perature in the extractor of between 10 and 40° C.; b) a counter-current liquid-liquid back-extraction comprising a back-extraction section supplied at the top with an acidic aqueous solution, having a pH between 0.5 and 5.0, and at the bottom with the extraction stream from step a), and producing at the top an extract and at the bottom the intermediate raffinate, wherein the back-extraction section is operated at a mean temperature between 40 and 80° C.

14 Claims, 1 Drawing Sheet

(56)             References Cited

FOREIGN PATENT DOCUMENTS

| | | |
|---|---|---|
| WO | 2018/001982 A1 | 1/2018 |
| WO | 2020/064317 A1 | 4/2020 |

OTHER PUBLICATIONS

Sulzer "Kuhni agitated columns (ECR)" Aug. 17, 2012; pp. 1-13 (Year: 2012).*
Zulawinska, J. "pH calculator" Jan. 7, 2025 (Year: 2025).*
International Search Report dated Jun. 2, 2020 issued in corresponding PCT/EP2020/059739 application (3 pages).

* cited by examiner

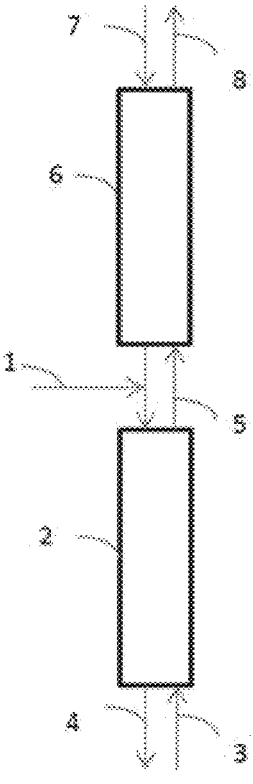

METHOD FOR PURIFYING AN AQUEOUS-ALCOHOLIC FEEDSTOCK COMPRISING ETHANOL AND ACETALDEHYDE

TECHNICAL FIELD

The present invention relates to a process for the treatment of a feedstock comprising at least water, ethanol and acetaldehyde, by liquid-liquid extraction and back-extraction, making it possible to maximize the removal of impurities, in particular nonpolar impurities or impurities with low polarity, while optimizing the recovery of the ethanol and the acetaldehyde.

The process according to the invention can advantageously be integrated in a more general process for the conversion of ethanol into butadiene, also called the Lebedev process. It then makes it possible to purify the liquid effluent resulting from the conversion reactors while improving the recovery of the ethanol and of the acetaldehyde not converted into butadiene.

PRIOR ART

The process for producing butadiene from ethanol was developed in particular by American teams during the Second World War starting from the studies of Ostromilenski.

In this process, the conversion per pass is less than 50%, which implies significant recyclings of the ethanol and acetaldehyde. Furthermore, a great variety of impurities of different natures (saturated, unsaturated or aromatic hydrocarbons, oxygen-based products, such as alcohols, ketones, aldehydes, phenols, acids, esters or ethers) and having very different molar masses is produced (between 50 and 10 000 g/mol).

It is thus necessary to put in place a line of unit operations with the aim of removing as many impurities as possible while losing as little ethanol and acetaldehyde as possible. From an economic viewpoint, it is essential to reduce the production cost of butadiene, which requires:

a) losing as little ethanol and acetaldehyde as possible, b) not recycling impurities in the reactors, which impurities would result in a fall in selectivity for butadiene or would accumulate at unacceptable levels, requiring a purge and thus losses of ethanol and acetaldehyde.

At the outlet of the catalytic reactors, the produced effluent, that comprises butadiene, ethanol, water, acetaldehyde and impurities, undergoes several unit operations in order to separate the undesired gaseous and liquid byproducts from the butadiene formed and from the compounds ethanol, water or acetaldehyde, called "noble" compounds, wherein liquid and gaseous are understood at ambient temperature and pressure.

Among the byproducts which are gaseous at ambient temperature and pressure, hydrogen, carbon monoxide, carbon dioxide and $C_1$-$C_4$ olefins and alkanes may be mentioned. It is essential to remove these byproducts from the effluent rich in butadiene in order to obtain a butadiene product with the required specifications. Among the byproducts which are liquid at ambient temperature and pressure, acetone, diethyl ether, butanal, butanol, butanone, ethyl acetate, crotonaldehyde and acetic acid may be mentioned. Other byproducts can be generated in a smaller amount in the reaction zone. In the continuation of the document, the term "impurities" will denote this combination of thousands of hydrocarbon or oxygen-based compounds.

In the first process schemes of the American teams, ethanol, acetaldehyde, water and the liquid byproducts are separated by a line of three distillation columns (U.S. Pat. No. 2,403,742). The effluent rich in ethanol, acetaldehyde, water and liquid byproducts feeds a first distillation column in which an effluent rich in acetaldehyde is separated from the remainder of the effluent. A second distillation column makes it possible to separate the liquid byproducts from an effluent rich in ethanol and water. The final distillation column makes it possible to separate the ethanol from the water. Most of the process patents filed in the period 1940-1960 by Carbide & Carbon or Koppers (U.S. Pat. Nos. 2,403,743, 2,393,381, 2,395,057 and 2,439,587) aim to improve this part of the scheme.

One of the problems of the process, observed in the years 1945, is a significant formation of diethyl acetal and/or ethyl hemiacetal resulting in particular from the reaction of ethanol with acetaldehyde, which results in a not insignificant loss of reactants (ethanol, acetaldehyde) and thus a fall in the butadiene yield. Toussaint et al., Industrial and Engineering Chemistry, 1947, Vol. 39, No. 2, pp. 120-125, indicate in particular that 20 kg of diethyl acetal are produced per tonne of butadiene formed.

In the patents FR 3 026 100 and FR 3 026 101, the liquid impurities are removed, at least in part, by liquid-liquid extraction. The liquid effluent at the outlet of the reactors, that comprises ethanol, acetaldehyde, water and impurities, feeds a liquid-liquid extraction column. The latter is fed at the bottom with a scrubbing solvent, the aim of which is to scrub the feedstock countercurrentwise. At the outlet of this scrubbing section, the extract is composed predominantly of the scrubbing solvent and of the extracted byproducts (such as diethyl ether) and comprises small amounts of ethanol and acetaldehyde. This extract is subsequently scrubbed with water with the aim of re-extracting the ethanol and the acetaldehyde and thus minimizing the losses of ethanol and acetaldehyde. The scrubbing solvent that is employed for this unit operation consists of a mixture of hydrocarbons having between 6 and 40 carbon atoms.

In this configuration, a high proportion of the diethyl acetal and ethyl hemiacetal, which are formed upstream of the liquid-liquid extraction step, in particular by reaction of the unconverted ethanol and of the unconverted acetaldehyde which are present in the liquid effluent at the outlet of the reactors, are extracted by the scrubbing solvent. This has the consequence of resulting in a not insignificant loss of ethanol and acetaldehyde equivalent and thus of increasing the cost of butadiene production.

The patent FR 3 057 467 provides, for its part, a process for the purification of the liquid effluent comprising ethanol, water and acetaldehyde from the Lebedev process described in particular in the patent FR 3 026 100 or FR 3 026 101, by liquid-liquid extraction and back-extraction with decomposition of the diethyl acetal that is catalyzed by the presence of an acid in the aqueous back-extraction solvent during the back-extraction step. However, such a process with the use of an acid dissolved in the aqueous phase results in a consumption and thus a more or less significant loss of acid molecules introduced in the back-extraction solvent.

The process according to the invention aims to limit this problem of acid consumption. More generally, the present invention aims for the purification of a hydroalcoholic feedstock comprising ethanol and acetaldehyde, while maximizing the removal of impurities, in particular nonpolar impurities or impurities with low polarity, contained in this aqueous feedstock and limiting the losses of ethanol and acetaldehyde. When it is advantageously integrated in a process of Lebedev type, such as that described in the patent FR 3 026 100 or the patent FR 3 026 101, the object of the present invention is to purify the liquid effluent resulting from the step of separation of the butadiene at the outlet of the reactors, and more particularly ethanol/acetaldehyde/ water effluent resulting from D1) of the patent FR 3 026 100 or ethanol/acetaldehyde/water effluent resulting from step B) of the patent FR 3 026 101, by maximizing the removal of impurities, in particular nonpolar impurities or impurities with low polarity (such as diethyl ether), contained in said liquid effluent while optimizing the amounts of unconverted ethanol and unconverted acetaldehyde, which are recycled to the reactors, this being achieved while minimizing the acid consumption. The present invention thus makes possible the improvement in the overall yield of the Lebedev process for converting ethanol to butadiene, with a reduced consumption of acid.

SUMMARY OF THE INVENTION

The invention relates to a process for the purification of a hydroalcoholic feedstock (1) comprising at least water, ethanol, acetaldehyde and impurities, said process comprising:

a) a step of countercurrentwise liquid-liquid extraction, comprising an extraction section comprising an extractor (2) that is fed at the top by said hydroalcoholic feedstock (1) and at least a fraction of an intermediate raffinate resulting from the back-extraction step b) and at the bottom by an extraction solvent (3), and that produces at the top an extraction stream (5) and at the bottom a raffinate (4) comprising water, ethanol and acetaldehyde, wherein said extraction section is operated at a mean temperature in the extractor of between 10 and 40° C.;

b) a step of countercurrentwise liquid-liquid back-extraction comprising a back-extraction section comprising a back-extractor (6) that is distinct from the extractor of step a) and fed at the top by an acidic aqueous solution (7), having a pH of between 0.5 and 5.0, and at the bottom by the extraction stream (5) resulting from step a), and that produces at the top an extract (8) and at the bottom said intermediate raffinate, wherein said back-extraction section is operated at a mean temperature in the back-extractor that is distinct from the mean temperature in the extractor of step a) and of between 40 and 80° C.

The invention relates to a line of unit operations for the extraction of impurities and the decomposition of the diethyl acetal and/or ethyl hemiacetal contained in a feedstock composed of water, ethanol, acetaldehyde and impurities, in particular a feedstock of Lebedev type.

Surprisingly, the applicant has discovered that, by imposing a particular liquid-liquid extraction/back-extraction system comprising two distinct columns and by controlling a certain number of operating parameters, such as the extraction and back-extraction temperatures, in addition to the pH of the aqueous solution used to carry out the re-extraction step, the extraction of impurities, in particular nonpolar impurities or impurities with low polarity, from the hydroalcoholic feedstock is maximized, the re-extraction of diethyl acetal and ethyl hemiacetal is optimized and thus the losses of ethanol and acetaldehyde are limited, with a reduced consumption of acid used to acidify the aqueous back-extraction solvent.

Advantageously, the process according to the invention is integrated in a Lebedev process (or process of Lebedev type), that is to say a process for the conversion of ethanol to butadiene, in particular to 1,3-butadiene. When it is advantageously integrated in a process of Lebedev type, such as that described in the patent FR 3 026 100 or FR 3 026 101, the process according to the invention thus makes it possible to efficiently purify, by a relatively simple liquid-liquid extraction/back-extraction method, the hydroalcoholic effluent obtained after separation of the butadiene from the effluent directly resulting from the conversion reactors, while reducing the losses of unconverted reactants, and thus to improve the performances of the process for the production of butadiene from ethanol, while reducing the operating costs thereof.

DESCRIPTION OF THE EMBODIMENTS

According to the invention, the compound 1,1-diethoxyethane, also called diethyl acetal, ethylidene diethyl ether or acetaldehyde diethyl acetal, is denoted, in the present description, diethyl acetal or DEA. It can be defined, according to the present invention, as a condensed form of ethanol with acetaldehyde. The corresponding hemiacetal is 1-ethoxyethan-1-ol or acetaldehyde ethyl hemiacetal and is called, in the present description, ethyl hemiacetal or EHA.

According to the present invention, "mean temperature" in the extraction section or the back-extraction section is a temperature calculated according to the arithmetic mean of at least two temperature values given by thermocouples distributed evenly throughout the extractor (or back-extractor) or the temperature determined using a thermocouple located at the center of the extractor (or back-extractor). For example, in the case where there are two thermocouples for determining the mean temperature in the extraction column, one thermocouple is placed in the upper half of the column and the second in the lower half, and preferably so that the thermocouple of the upper part of the column is at a distance from the top of the extraction column equal to that between the thermocouple of the lower part and the bottom of the extraction column. The greater the number of thermocouples arranged evenly throughout the extractor (or back-extractor), the more accurate the mean temperature in the extractor (or back-extractor).

According to the present invention, the expression "of between . . . and . . . " means that the limit values of the interval are included in the range of values which is described. If such were not the case and if the limit values were not included in the described range, such a detail will be provided by the present invention.

The invention relates to a process for the purification of a hydroalcoholic feedstock comprising at least water, ethanol, acetaldehyde and impurities, said process comprising, preferably consisting of, the following steps:

a) a step of countercurrentwise liquid-liquid extraction, comprising an extraction section comprising an extractor (2) that is fed at the top by said hydroalcoholic feedstock (1) and at least a fraction of an intermediate raffinate resulting from the back-extraction step b) and at the bottom by an extraction solvent (3), and that produces at the top an extraction stream (5) and at the bottom a raffinate (4) comprising water, ethanol and acetaldehyde, wherein said extraction section is operated at a mean temperature in the extractor of between 10 and 40° C.;

b) a step of countercurrentwise liquid-liquid back-extraction comprising a back-extraction section comprising a back-extractor (6) that is distinct from the extractor of step a) and fed at the top by an acidic aqueous solution (7), having a pH of between 0.5 and 5.0, and at the bottom by the extraction stream (5) resulting from step a), and that produces at the top an extract (8) and at the bottom said intermediate raffinate, wherein said back-extraction section is operated at a mean temperature in the back-extractor that is distinct to the mean temperature in the extractor of step a) and of between 40 and 80° C.

The Hydroalcoholic Feedstock:

The process according to the invention makes it possible to extract the ethanol and the acetaldehyde from a hydroalcoholic feedstock comprising water, ethanol and acetaldehyde. Said hydroalcoholic feedstock also comprises impurities, in particular organic impurities, which can be of highly varied natures, for example saturated, unsaturated or aromatic hydrocarbons, oxygen-based products, among which may be mentioned alcohols, ketones, aldehydes, phenolic compounds, acids, esters or ethers, wherein the molar masses of the various impurities may range from 50 to 10 000 g/mol. Typically, the impurities can be acetone, diethyl ether, butanal, butanols, butanones, ethyl acetate, crotonaldehyde, pentenes, pentadienes, hexenes and hexadienes.

The hydroalcoholic feedstock in the process according to the invention can optionally also comprise at least one acetal and/or hemiacetal. In particular, the hydroalcoholic feedstock to be treated can comprise diethyl acetal and/or ethyl hemiacetal. Diethyl acetal and ethyl hemiacetal are known to be the products of the reaction of ethanol with acetaldehyde.

According to the invention, the term "impurities" thus denotes any compounds, in particular organic compounds, other than water, ethanol and acetaldehyde and other than acetals and hemiacetals, in particular other than diethyl acetal and ethyl hemiacetal. The impurities can, for example, be saturated, unsaturated or aromatic hydrocarbons, such as pentenes, pentadienes, hexenes and hexadienes, or oxygen-based products, such as acetone, diethyl ether, butanal, butanols, butanones, ethyl acetate or crotonaldehyde.

In particular, some of the impurities can be considered as nonpolar with low polarity, when they exhibit with a partition coefficient, in particular by weight, between the organic extraction phase and the aqueous extraction phase, preferably of greater than or equal to 1, preferentially of greater than or equal to 2.

The purification process according to the invention is thus advantageously fed by a hydroalcoholic feedstock comprising at least water, ethanol, acetaldehyde, impurities and optionally acetals and/or hemiacetals, in particular diethyl acetal and/or ethyl hemiacetal.

Preferably, the hydroalcoholic feedstock comprises between 30% and 70% by weight of ethanol, preferably between 40% and 60% by weight of ethanol, with respect to the total weight of the hydroalcoholic feedstock, between 1% and 30% by weight of acetaldehyde, preferably between 5% and 10% by weight of acetaldehyde, with respect to the total weight of the hydroalcoholic feedstock, and between 0.5% and 20% by weight of impurities, in particular between 1% and 20% by weight of impurities, with respect to the total weight of the hydroalcoholic feedstock. When the feedstock additionally comprises at least one acetal and/or hemiacetal, such as diethyl acetal and/or ethyl hemiacetal, the content by weight of acetals and hemiacetals in said hydroalcoholic feedstock is preferably of between 1% and 20% by weight, and preferably between 1% and 15% by weight.

Advantageously, said hydroalcoholic feedstock results from the conversion of ethanol to butadiene, in particular to 1,3-butadiene, after separation of the noncondensables and of the butadiene. Said hydroalcoholic feedstock is preferably a hydroalcoholic effluent resulting from a step of separation of the butadiene at the outlet of the conversion reactors in a Lebedev process, for example an effluent similar to the ethanol/acetaldehyde/water effluent resulting from D1) of the patent FR 3 026 100 or the ethanol/acetaldehyde/water effluent resulting from step B) of the patent FR 3 026 101.

Step a) of Extraction of the Impurities:

In accordance with the invention, the purification process according to the invention comprises a step a) of countercurrentwise liquid-liquid extraction, comprising an extraction section comprising an extractor (2) that is fed at the top by said hydroalcoholic feedstock (1) and at least a fraction of the intermediate raffinate resulting from the back-extraction step b) and at the bottom by an extraction solvent (3), and that produces at the top an extraction stream (5), also called intermediate extract, and at the bottom a raffinate (4) comprising water, ethanol and acetaldehyde, also called hydroalcoholic raffinate.

According to the invention, said extraction section is operated at a mean temperature in the extractor of between 10 and 40° C., preferably between 15 and 30° C. If the mean temperature in the extractor is less than 10° C. or greater than 40° C., the extraction of the impurities, in particular nonpolar impurities or impurities with low polarity, is less efficient.

The extraction solvent and the hydroalcoholic feedstock which feed said extraction section of step a) are advantageously each independently at an inlet temperature of between 10 and 40° C.

Advantageously, the pressure of said extraction section of step a) is adjusted so that the various streams passing through said section remain in liquid form. Preferably, said extraction section of step a) is operated at a pressure of between 0.1 and 0.5 MPa, preferentially between 0.2 and 0.4 MPa.

The residence time in the extraction section of said step a) is advantageously adjusted so as to obtain the desired performances in terms of degree of recovery, as is known to a person skilled in the art. In particular, the residence time in the extraction section of said step a) is of between 0.5 and 10.0 h, preferably between 0.5 and 8.0 h, in a preferred way between 1.0 and 6.0 h. The residence time in the extraction section is defined as a residence time of the aqueous phase and corresponds to the ratio of the total volume occupied by the aqueous phase under consideration in the extraction section with respect to the flow rate by volume of this aqueous phase at the outlet of the extraction section.

According to the invention, the extraction solvent which feeds step a) is advantageously an organic solvent, preferably a nonpolar organic solvent. Preferably, the extraction solvent which feeds step a) is a mixture of hydrocarbons having between 6 and 40 carbon atoms, preferably between 10 and 20 carbon atoms, or any other solvent which allows a demixing with the hydro-alcoholic phase. In a nonlimiting way, said mixture of hydrocarbons can be a desulfurized gas oil or kerosene cut or alternatively a hydrocarbon cut produced by a unit of Fischer-Tropsch type. Preferably, the extraction solvent which feeds step a) is hexadecane.

It is well known to a person skilled in the art that a liquid-liquid extraction, in particular a countercurrentwise liquid-liquid extraction, operates with two liquid phases, one of the phases constituting the continuous phase and the other constituting the dispersed phase that is present in the form of distinct drops. The continuous or dispersed nature depends on the relative flow rate of one phase with respect to the other. According to the well-known phenomenon, the nature of the dispersed phase and of the continuous phase depends on the relative flow rates of these phases. Thus, if the flow rate of the continuous phase is reduced by increasing the flow rate of the dispersed phase, the dispersed phase will become continuous, and vice versa. Advantageously, the extraction section is operated with a ratio of flow rate by weight of continuous phase with respect to the flow rate by weight of dispersed phase of less than 70, preferably of less than 35, in a preferred way of less than 10, and preferably of less than 3, preferably of less than 1.5. Above 70, the hydrodynamic functioning of the extraction section is compromised. It does not matter whether the extraction solvent (organic phase) forms the continuous or dispersed phase, this criterion being a hydrodynamic criterion. Preferably, in the extraction step a), the continuous phase is the organic phase and the dispersed phase is the aqueous phase.

The higher the ratio of flow rate by weight of extraction solvent (that is to say, flow rate by weight of extraction solvent entering the extraction section) with respect to the flow rate by weight of the feed of said extraction section of said step a), composed of the hydroalcoholic feedstock and at least a fraction of the intermediate raffinate resulting from the back-extraction step b), the more efficient the step a) of impurities extraction. However, high ratio of the flow rates also leads to extract a large fraction of ethanol and acetaldehyde in the extraction stream produced at the top of the extraction section of step a), and consequently to increase the flow rate of aqueous solution necessary during step b) in order to limit the losses of ethanol and acetaldehyde. The value of the ratio of flow rate by weight of extraction solvent to the flow rate by weight of aqueous feedstock thus has to be adjusted so as to extract the maximum of impurities, in particular nonpolar impurities or impurities with low polarity, while limiting the losses of ethanol and acetaldehyde. The ratio of the flow rate by weight of extraction solvent with respect to the flow rate by weight of feedstock for feeding step a), composed of the hydroalcoholic feedstock and of at least a fraction of the intermediate raffinate resulting from step b), is preferably of between 0.1 and 5.0, preferentially between 0.2 and 2.0, in a preferred way between 0.3 and 1.0.

The flow rate by weight of extraction solvent and also the flow rate by weight of acidic aqueous solution (that is to say, the flow rate by weight of back-extraction solvent) feeding step b) are advantageously adjusted so that the extract produced during step b) comprises at least 50% by weight, preferably at least 60% by weight, in a preferred way at least 70% by weight, in a very preferred way at least 80% by weight, indeed even at least 90% by weight, of the nonpolar impurities or impurities with low polarity contained in the hydroalcoholic feedstock that feeds said step a) of the process according to the invention, and at most 5% by weight, preferably at most 2% by weight and in a preferred way at most 1% by weight of the total amount by weight of ethanol and acetaldehyde (in free and/or condensed form, for example in the form of diethyl acetal and/or ethyl hemiacetal) contained in said hydroalcoholic feedstock feeding said step a). Preferably, the ratio of the flow rate by weight of the acidic aqueous solution (that is to say, the flow rate by weight of back-extraction solvent) feeding step b) with respect to the flow rate by weight of extraction solvent feeding step a) is of between 0.1 and 5.0, preferably between 0.2 and 2.0, preferentially between 0.3 and 1.0, in a preferred way between 0.4 and 0.5.

The contact between the two liquid phases in said extraction section of step a) is advantageously carried out within an extractor. Different extractor technologies can be envisaged: the extractor can, for example, be a packed column, a plug-flow column, a stirred compartmentalized column, compartmentalized using perforated plates, using disks or using rings, or else a battery of mixer-settlers or mixer-centrifuges. Preferably, the extractor is a plug-flow column or a stirred compartmentalized column. Advantageously, the extractor used in the extraction step a) comprises between 1 and 20, preferentially between 2 and 8, theoretical extraction stages.

The intermediate extract (or extraction stream) (5), which is produced at the top of said extraction section of step a) of the process according to the invention, advantageously comprises at least 50% by weight, preferably at least 60% by weight, in a preferred way at least 70% by weight and very preferably at least 80% by weight of the nonpolar impurities or impurities with low polarity from the hydroalcoholic feedstock. Said intermediate extract (5) comprises ethanol and acetaldehyde present in the hydroalcoholic feedstock which feeds the process according to the invention, in their free and/or condensed form. Thus, the intermediate extract (5) produced at the top of the extraction section in step a) very probably comprises diethyl acetal and/or ethyl hemiacetal, that are possibly included in the hydroalcoholic feedstock feeding the process according to the invention and/or formed by reaction of ethanol with acetaldehyde during the process according to the invention, in particular in said extraction section in step a).

The hydroalcoholic raffinate (4) produced at the bottom of the extraction section of said step a) comprises water and between 80% and 100% by weight of the total amount of ethanol and acetaldehyde contained in said hydroalcoholic feedstock feeding the process according to the invention. In other words, between 80% and 100% by weight of the total amount of ethanol and acetaldehyde of the hydroalcoholic feedstock feeding the process according to the invention are recovered in the hydroalcoholic raffinate (4) that is produced at the bottom of the extraction section of step a) of the process according to the invention.

Step a) of the process according to the invention is configured so as to extract the maximum of impurities, in particular nonpolar impurities or impurities with low polarity (such as diethyl ether), and the minimum of ethanol and acetaldehyde (in free and/or condensed form).

In such a configuration, the acetals and/or hemiacetals, in particular diethyl acetal and/or ethyl hemiacetal, that are possibly present in the hydroalcoholic feedstock and/or formed during the process according to the invention, in particular during the extraction step a), are significantly extracted by the extraction solvent into the extraction stream, with the impurities, in particular nonpolar impurities or impurities with low polarity, during the extraction step a), insofar as said acetals and/or hemiacetals are much less polar than free ethanol and free acetaldehyde. The extraction stream (5) extracted at the top of the extraction section of said step a) feeds the back-extraction step b).

Back-Extraction Step b):

In accordance with the invention, the purification process comprises a step b) of countercurrentwise liquid-liquid back-extraction, the objective of which is to efficiently back-extract the noble compounds, that is to say ethanol and acetaldehyde in free form and/or condensed form as ethyl hemiacetal or diethyl acetal.

According to the invention, step b) of countercurrentwise liquid-liquid back-extraction comprises a back-extraction section comprising a back-extractor (6) that is distinct from the extractor (2) of step a), that is fed at the top by an acidic aqueous solution (7), having a pH of between 0.5 and 5.0, and at the bottom by the extraction stream (5) resulting from step a), and that produces at the top an extract (8) and at the bottom an intermediate raffinate.

The back-extraction section is, according to the invention, operated at a mean temperature in the back-extractor that is distinct from the mean temperature in the extractor of step a) and of between 40 and 80° C., preferably of between 45 and 70° C., preferably between 45 and 60° C. Very preferably, the extraction section in step a) is operated at a mean temperature in the extractor of between 15 and 30° C. and the back-extraction section in step b) is operated at a mean temperature in the back-extractor of between 45 and 70° C., in particular between 45 and 60° C. For mean temperature values in the back-extraction section of greater than 80° C., there is, in addition to an increase in the production cost generated by an increase in the energy consumption required for the heating, a risk of formation of bubbles in the aqueous and organic phases, bringing in a loss in back-extraction efficiency. When the mean temperature in the back-extraction section is less than 40° C., the back-extraction efficiency appears nonoptimal. Said acidic aqueous solution and the extraction stream resulting from step a) advantageously feed said back-extraction section of step b) each independently at an inlet temperature of between 10 and 90° C., preferably between 40 and 90° C.

According to a specific embodiment of the invention, the back-extraction section comprises an adiabatic column (called insulated column), as back-extractor, that is fed at the top with the acidic aqueous solution at an inlet temperature of said acidic aqueous solution into said adiabatic column of between 50 and 90° C., preferably between 60 and 85° C., and at the bottom by the extraction stream resulting from step a). The inlet temperature of the extraction stream resulting from step a) into said adiabatic column is set by the temperature at which the extraction step a) is carried out, i.e. on average between 10 and 40° C. In this specific embodiment of the invention, a temperature gradient that is generated between the top of the column and the bottom makes it possible to obtain a mean temperature in the adiabatic back-extraction column which is distinct from the mean temperature in the extraction section of step a), that is sufficiently high, advantageously of between 40 and 80° C., to obtain the desired effects, that is to say an optimized re-extraction of the ethanol and acetaldehyde and/or of the diacetals and hemiacetals contained in the extraction stream resulting from step a).

Advantageously, the pressure in said back-extraction section is adjusted so that the various streams passing through said section remain in liquid form. Preferably, the back-extraction section of step b) is operated at a pressure of between 0.1 and 0.5 MPa, preferentially between 0.2 and 0.4 MPa.

Advantageously, the back-extraction section of step b) is operated with a residence time, more precisely a residence time in the aqueous phase, in the back-extraction section of between 0.5 and 10.0 h, preferentially between 0.5 and 8.0 h, in a preferred way between 1 and 6.0 h. Said residence time in the back-extraction section is defined as the mean time required for a water molecule injected with the acidic aqueous solution feeding said back-extraction section of said step b) to be extracted in the intermediate raffinate resulting from said back-extraction section of said step b). This residence time is conventionally determined by measurement of RTD or Residence Time Distribution, in which a marker (colorant or other) is injected from time to time at the inlet, the concentration of marker being observed at the outlet.

According to the invention, the back-extraction solvent used in step b) is an acidic aqueous solution having a pH between 0.5 and 5.0, preferably between 2 and 4.0 and in a preferred way between 2.5 and 3.5. Said acidic aqueous solution which feeds step b) is advantageously water that is acidified by addition of an acidic compound so that the pH of the aqueous solution is of between 0.5 and 5.0, preferably between 2 and 4.0 and in a preferred way between 2.5 and 3.5. The acidic aqueous solution can thus contain, without limitation, strong acids and/or weak acids. Without limitation, the water is acidified with a weak acid, such as acetic acid, or a strong acid, such as sulfuric acid or nitric acid, preferably with acetic acid. Preferably, the acidic aqueous solution is water acidified with acetic acid, so that said acidic aqueous solution comprises a content of acetic acid of less than 3% by weight of acetic acid, preferably of less than or equal to 3.0% by weight, in a preferred way of less than or equal to 1.5% by weight, with respect to the total weight of said acidic aqueous solution.

In addition, said acidic aqueous solution which feeds step b) preferably contains less than 2% by weight, in a preferred way less than 1% by weight, of the total amount of ethanol and acetaldehyde, with respect to the total weight of said acidic aqueous solution, that is to say that the sum of the contents by weight of ethanol and acetaldehyde in said acidic aqueous solution is less than 2% by weight, preferably less than 1% by weight, with respect to the total weight of said acidic aqueous solution. Very preferably, said acidic aqueous solution contains neither ethanol nor acetaldehyde.

The contact between the two liquid phases, the organic phase and aqueous phase, in said back-extraction section of step b) is advantageously carried out within a back-extractor. Different technologies for said back-extractor can be envisaged: packed column, plug-flow column, stirred compartmentalized column, compartmentalized using perforated plates, using disks or using rings, or else a battery of mixer-settlers or mixer-centrifuges. Preferably, the back-extractor is a plug-flow column or a stirred compartmentalized column. Advantageously, the back-extractor used in the back-extraction step b) comprises between 1 and 20, preferentially between 1 and 5, theoretical stages.

Advantageously, the flow rates by weight of the aqueous phase and the organic phase in the back-extraction section are adjusted so that the ratio ($Q_{aq.\ entering}/Q_{orga.\ exiting}$) of the flow rate by weight of the aqueous phase entering the back-extraction section ($Q_{aq.\ entering}$) with respect to the flow rate of the organic phase exiting the back-extraction section ($Q_{orga.\ exiting}$) is preferably between 0.1 and 5.0, preferentially between 0.2 and 2.0, in a preferred way between 0.3 and 1.0.

Preferably, step b) is carried out so that the aqueous phase constitutes the continuous phase in the back-extraction section and the organic phase constitutes the dispersed phase in said back-extraction section of said step b).

Very advantageously, the aqueous phase constitutes the dispersed phase in the extraction section of step a) and the continuous phase in the back-extraction section of step b).

Under such operating conditions, the acetals and/or hemiacetals, in particular diethyl acetal and/or ethyl hemiacetal, that are possibly present in the hydroalcoholic feedstock and/or formed during the process according to the invention, in particular by reaction between ethanol and acetaldehyde, decompose especially into ethanol and acetaldehyde, which can be re-extracted into the aqueous phase of the back-extraction section, preferably the continuous phase of the back-extraction section, thus making it possible to improve the recovery of the losses in ethanol and acetaldehyde. This decomposition thus makes it possible, when the purification process according to the invention is integrated in a Lebedev process, to limit the losses of reactants and consequently to improve the butadiene yield of the Lebedev process overall.

The back-extraction step b) of the process according to the invention produces, at the top of the back-extraction section, an extract (8) that advantageously comprises at least 50% by weight, preferably at least 60% by weight, in a preferred way at least 70% by weight, very preferably at least 80% by weight, indeed even at least 90% by weight, of the impurities, in particular nonpolar impurities or impurities with low polarity, of the hydroalcoholic feedstock feeding step a) of the process according to the invention. The extract (8) produced at the top of the back-extraction section of step b) advantageously comprises less than 1.0% by weight, preferably less than 0.1% by weight, in a preferred way less than 0.001% by weight of acetals and/or hemiacetals, in particular of diethyl acetal and/or ethyl hemiacetal. Very preferably, the extract produced at the top of the back-extraction section of step b) is free from acetals and/or hemiacetals, in particular free from diethyl acetal and/or ethyl hemiacetal.

The extract resulting from step b) can subsequently be treated, for example, in a purification/separation step in order to recover the extraction solvent in order to be able to recycle it to the extraction step a).

The back-extraction section of step b) produces at the bottom an intermediate raffinate that advantageously comprises water, ethanol and acetaldehyde. At least a fraction of said intermediate raffinate, advantageously said the entire intermediate raffinate, is introduced at the top of the extraction section of step a). Even when the entire intermediate raffinate is introduced into the extraction section, a withdrawal can advantageously be carried out continuously or noncontinuously on said intermediate raffinate, said withdrawal being called purge, in order to limit the accumulation of the impurities in this intermediate raffinate.

Surprisingly, the applicant has discovered that, by operating the extraction (or scrubbing) and the back-extraction (or back-scrubbing) in two distinct extractors, by using an acidic aqueous solution as back-extraction solvent and by imposing two distinct temperatures in the two columns, the removal of the impurities, in particular nonpolar impurities or impurities with low polarity, from the hydroalcoholic feedstock to be treated, for example liquid effluent resulting from the reactors for the conversion of ethanol into butadiene, as in a Lebedev process, was very efficient while the losses of ethanol and acetaldehyde were surprisingly limited and the consumption of acid, necessary to acidify the back-extraction water, substantially reduced.

Advantageously, the process according to the invention makes it possible to achieve an efficiency of extraction of the nonpolar impurities or impurities with low polarity, in particular an efficiency of extraction of diethyl ether, of greater than or equal to 75% by weight, preferably of greater than or equal to 80% by weight, and an efficiency of back-extraction, in particular of diethyl acetal, condensed form of ethanol and acetaldehyde, of greater than or equal to 90% by weight, preferably of greater than or equal to 95% by weight and in a preferred way of greater than or equal at 97% by weight.

The term "efficiency of extraction" means, according to the invention, the efficiency of extraction of diethyl ether, defined by the ratio ($Q_{DEE\ extract}$/$Q_{DEE\ entering}$) of the flow rate by weight of diethyl ether (DEE) exiting the process, that is to say present in the extract obtained at the top of the back-extraction section ($Q_{DEE\ extract}$), to the flow rate by weight of diethyl ether (DEE) entering the extraction section, that is to say present in the hydroalcoholic feedstock feeding the extraction section ($Q_{DEE\ entering}$). More particularly, the efficiency of extraction of the diethyl ether (DEE) is calculated in the following way: Efficiency of extraction DEE=[(weight content of DEE of the extract exiting the top of the back-extraction section)×(flow rate by weight of the extract exiting the top of the back-extraction section)/ (weight content of DEE of the hydroalcoholic feedstock)× (flow rate by weight of the hydroalcoholic feedstock)].

The term "efficiency of back-extraction" means the efficiency of extraction of the diethyl acetal, defined by the ratio of the amount by weight of diethyl acetal back-extracted from the intermediate extract to the amount by weight of diethyl acetal present in the intermediate extract entering the back-extraction section. More particularly, the efficiency of back-extraction of the diethyl acetal (DEA) is calculated in the following way: Efficiency of back-extraction DEA=1– [(weight content of DEA of the extract exiting the top of the back-extraction section)×(flow rate by weight of the extract exiting the top of the back-extraction section)/(weight content of DEA of the intermediate extract entering the back-extraction section)×(flow rate by weight of the intermediate extract entering the back-extraction section)].

The weight contents of DEE and of DEA of the various considered streams in order to calculate the extraction and back-extraction efficiencies are determined by any method known to a person skilled in the art, for example by gas chromatography.

The purification process according to the invention can advantageously be integrated in an overall process of Lebedev type, that is to say an overall process for converting ethanol to butadiene, as a step of purification of the hydroalcoholic liquid effluent resulting from a step of separation of the butadiene at the outlet of the reactors for the conversion of ethanol to butadiene. This is because, in a process of Lebedev type, the hydroalcoholic liquid effluent resulting from the step of separation at the outlet of the reactors for converting ethanol to butadiene comprises water, originating in particular from the conversion of ethanol to butadiene, and reactants, ethanol and acetaldehyde, which are unconverted or only partially converted. Said hydroalcoholic liquid effluent also comprises impurities consisting of organic molecules, such as acetone, diethyl ether, butanal, butanols, butanones, ethyl acetate, crotonaldehyde, pentenes, pentadienes, hexenes or hexadienes, and optionally acetals and/or hemiacetals, in particular diethyl acetal and/or ethyl hemiacetal. When the treatment process according to the invention is integrated in a process of Lebedev type, the rate of recycling of the reactive compounds, that is to say ethanol and acetaldehyde, is improved, thus allowing an optimization of the overall yield of butadiene of the Lebedev process, this being achieved without generating an additional cost, which might be due to consumption of acidic compound, or post-treatment of the aqueous phase.

The FIGURES incorporated in the present description and the examples which follow are presented by way of illustration and without limitation of the purification process according to the invention.

LIST OF THE FIGURES

The FIGURE diagrammatically and nonlimitingly represents an arrangement of the process according to the invention. The hydroalcoholic feedstock comprising water, ethanol, acetaldehyde and impurities (1) feeds, at the top, a liquid-liquid extraction section (2) in which step a) is carried out. The liquid-liquid extraction section (2) is also fed at the top by an intermediate raffinate resulting from the back-extraction section (6) of step b) and at the bottom by an extraction solvent (3). An extraction stream (5), also called intermediate extract, is produced at the top of the extraction section (2) while a raffinate (4) is withdrawn at the bottom of the extraction section (2). The extraction stream (5) feeds, at the bottom, the back-extraction section (6) of step b). The back-extraction section (6) is fed, at the top, by an acidic aqueous solution (7). An extract (8) is withdrawn at the top of the back-extraction section (6) while at the bottom an intermediate raffinate is produced. Said intermediate raffinate feeds the liquid-liquid extraction section (2).

EXAMPLES

In the following examples, an hydroalcoholic feedstock comprising ethanol, acetaldehyde, water and impurities, in particular nonpolar impurities or impurities with low polarity, such as diethyl ether (regarded as an impurity), with a composition given in table 1 and with a flow rate by weight of 3.65 kg/hour, is treated.

| Compounds | Weight Content (% by weight with respect to the total weight of the feedstock) |
|---|---|
| Acetaldehyde | 3.91% |
| Ethanol | 62.95% |
| Acetone | 0.07% |
| Ethyl vinyl ether | 0.04% |
| Diethyl ether | 1.00% |
| Butanal | 0.03% |
| Butanone | 0.01% |
| Ethyl acetate | 1.37% |
| Acetic acid | 0.63% |
| Butanol | 0.41% |
| Diethyl acetal | 4.46% |
| Styrene | 0.10% |
| Water | 25.01% |

In the following examples, the extraction and back-extraction sections are operated under the same following conditions; only the mean temperatures of the extraction and back-extraction sections and the weight content of acetic acid of the acidic aqueous solution used as back-extraction solvent differ.

The extraction and back-extraction columns are distinct columns, both of ECR Sulzer type with internals having plate openings of 40%, with an internal diameter of 32 mm and a working height of 1.8 m.

The extraction column is fed at the bottom with hexadecane at a flow rate of 1.28 kg/hour. The back-extraction column is fed at the top with water acidified by acetic acid, the flow rate of this back-extraction solvent being at 0.56 kg/hour.

The extraction column is operated in dispersed aqueous phase. The back-extraction column is operated in continuous aqueous phase.

The stirring speed is adjusted in both columns so that the fraction by volume of dispersed phase is approximately 15% by volume in the extraction column and 3% by volume in the back-extraction column.

The extraction column produces at the top an extraction stream which is injected at the bottom of the back-extraction column. The extraction column produces at the bottom a raffinate comprising ethanol and acetaldehyde. The back-extraction column produces at the top of the column an extract and at the bottom an intermediate raffinate, the latter being injected at the top of the extraction column.

In the various examples, the acetic acid concentration of the acidic aqueous solution (back-extraction solvent), thus the pH of this acidic aqueous solution, and also of the mean temperatures of the extraction and back-extraction sections vary. Table 2 below summarizes the variable operating conditions and the results obtained in terms of efficiency of extraction of the impurity diethyl ether and of efficiency of back-extraction of diethyl acetal.

The efficiency of extraction of diethyl ether (DEE) and the efficiency of back-extraction of diethyl acetal (DEA) are calculated, for each example, as presented above in the description, that is to say in the following way:

Efficiency of extraction of DEE=[(weight content of DEE of the extract)×(flow rate by weight of the extract)/(weight content of DEE of the hydroalcoholic feedstock)×(flow rate by weight of the hydroalcoholic feedstock)].

Efficiency of back-extraction DEA=1−[(weight content of DEA of the extract)×(flow rate by weight of the extract)/(weight content of DEA of the intermediate extract)×(flow rate by weight of the intermediate extract)].

The weight contents of DEE of the extract and of the hydroalcoholic feedstock and the weight contents of DEA of the extract and of the intermediate extract were determined by gas chromatography.

| Examples | Acetic acid content (% by weight) | pH of the acidic aqueous solution | Extraction temperature (° C.) | Back-extraction temperature (° C.) | Efficiency of extraction of DEE (% by weight) | Efficiency of back-extraction of DEA (% by weight) |
|---|---|---|---|---|---|---|
| 1 | 3% | 2.5 | 20 | 20 | 81% | 93% |
| 2 | 1% | 2.8 | 20 | 20 | 81% | 74% |
| 3 | 1% | 2.8 | 40 | 40 | 72% | 92% |
| 4 | 1% | 2.8 | 50 | 50 | 43% | 98% |
| 5 | 1% | 2.8 | 20 | 50 | 81% | 98% |

Example 1 illustrates the reference case in accordance with the prior art. With an acetic acid content of the back-extraction solvent of 3% by weight and an operating temperature equal to 20° C. for the two columns, the efficiency of extraction of diethyl ether (DEE) and the efficiency of back-extraction of diethyl acetal (DEA) are satisfactory, since respectively greater than 80% by weight (81% efficiency of extraction of DEE) and greater than 90% by weight (93% efficiency of back-extraction of DEA).

Example 2 shows that, at the same operating temperature as above (20° C. in both columns), when the acetic acid content in the acidic aqueous solution used as back-extraction solvent decreases (1% by weight instead of 3% by weight), the efficiency of back-extraction of DEA decreases substantially and becomes less than 75% by weight.

According to examples 3 and 4, the joint increase in the temperature in both columns (extraction and back-extraction), to 40° C. for example 3 and 50° C. for example 4, makes it possible to recover a satisfactory efficiency of back-extraction (92% and 98% respectively) for low acetic acid contents in the aqueous back-extraction solvent (1%). However, the effect on the extraction of DEE is detrimental since the efficiency of extraction of DEE becomes less than 75%: more precisely, the efficiency of extraction of DEE is 72% by weight in example 3 and 43% by weight in example 4.

Example 5, in accordance with the invention, clearly demonstrates that, even for a low content of acetic acid in the acidic aqueous solution used as back-extraction solvent, imposing two distinct temperatures between the extraction and the back-extraction, and in particular a temperature of 20° C. in the extraction column and a mean temperature of 50° C. in the back-extraction column, makes it possible to obtain an optimized extraction of DEE, with an efficiency of extraction of DEE equal to 81% by weight, and a high back-extraction of DEA, with an efficiency of back-extraction of DEA equal to 98% by weight, an efficiency of back-extraction which is greater than that obtained in example 1 according to the prior art.

It thus clearly appears that the process according to the invention, for purifying a hydroalcoholic feedstock comprising water, ethanol, acetaldehyde and impurities, makes it possible to extract the nonpolar impurities or impurities with low polarity in an optimal manner and to improve the back-extraction of the condensed form of ethanol and acetaldehyde, with a substantially reduced consumption of acetic acid.

The invention claimed is:

1. A process for the purification of a hydroalcoholic feedstock (1) comprising at least water, ethanol, acetaldehyde and impurities, said process comprising:

a) a step of countercurrentwise liquid-liquid extraction, comprising an extraction section comprising an extractor (2) that is fed at the top by said hydroalcoholic feedstock (1) and at least a fraction of an intermediate raffinate resulting from a countercurrentwise liquid-liquid back-extraction step b) and at the bottom by an extraction solvent (3), and that produces at the top an extraction stream (5) and at the bottom a raffinate (4) comprising water, ethanol and acetaldehyde, wherein said extraction section is operated at a mean temperature in the extractor of between 15 and 30° C.; and b) the step of countercurrentwise liquid-liquid back-extraction comprising a back-extraction section comprising a back-extractor (6) that is distinct from the extractor of step a) and fed at the top by an acidic aqueous solution (7), and at the bottom by the extraction stream (5) resulting from step a), and that produces at the top an extract (8) and at the bottom said intermediate raffinate, wherein said back-extraction section is operated at a mean temperature in the back-extractor that is distinct from the mean temperature in the extractor of step a) of between 4° and 80° C., wherein said acidic aqueous solution (7) comprises a content of acetic acid of less than or equal to 1.5% by weight of acetic acid with respect to the total weight of said acidic aqueous solution.

2. The process as claimed in claim 1, wherein the mean temperature in the extraction column (2) of step a) is 20° C.

3. The process as claimed in claim 1, wherein the mean temperature in the back-extraction column (6) of step b) is between 45 and 60° C.

4. The process as claimed in claim 1, wherein the back-extractor of step b) is an adiabatic column fed at the top by said acidic aqueous solution (7), at a temperature for entry of said acidic aqueous solution into said adiabatic column of between 5° and 90° C.

5. The process as claimed in claim 1, wherein the hydroalcoholic feedstock (1) comprises between 30% and 70% by weight of ethanol with respect to the total weight of the hydroalcoholic feedstock, between 1% and 30% by weight of acetaldehyde with respect to the total weight of the hydroalcoholic feedstock, and between 0.5% and 20% by weight of impurities with respect to the total weight of the hydroalcoholic feedstock.

6. The process as claimed in claim 1, wherein the hydroalcoholic feedstock (1) additionally comprises at least one acetal and/or hemiacetal.

7. The process as claimed in claim 1, wherein the hydroalcoholic feedstock (1) is an hydroalcoholic effluent resulting from a step of separation of butadiene at an outlet of a conversion reactor in a Lebedev process.

8. The process as claimed in claim 1, wherein the extraction solvent (3) is a nonpolar organic solvent.

9. The process as claimed in claim 8, wherein the extraction solvent (4) is hexadecane.

10. The process as claimed in claim 1, wherein said acidic aqueous solution (7) which feeds the back-extraction column (6) of step b) comprises less than 2% by weight of the ethanol and acetaldehyde combination.

11. The process as claimed in claim 1, wherein said acidic aqueous solution comprises a content of acetic acid of less than 1.5% by weight of acetic acid with respect to the total weight of said acidic aqueous solution.

12. The process as claimed in claim 8, wherein the extraction solvent (3) is a mixture of hydrocarbons having between 6 and 40 carbon atoms.

13. The process as claimed in claim 8, wherein the extraction solvent (3) is a mixture of hydrocarbons having between 10 and 20 carbon atoms.

14. The process as claimed in claim 1, wherein the mean temperature in the extraction column (2) of step a) is 20° C. and the mean temperature in the back-extraction column (6) of step b) is between 50 to 80° C.

* * * * *